(12) United States Patent
Chen

(10) Patent No.: US 10,036,725 B2
(45) Date of Patent: *Jul. 31, 2018

(54) NON-FARADAIC, CAPACITIVELY COUPLED MEASUREMENT IN A NANOPORE CELL ARRAY

(71) Applicant: Genia Technologies, Inc., Santa Clara, CA (US)

(72) Inventor: Roger J. A. Chen, Saratoga, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,107

(22) Filed: Oct. 7, 2016

(65) Prior Publication Data

US 2017/0153205 A1 Jun. 1, 2017

Related U.S. Application Data

(63) Continuation of application No. 14/056,795, filed on Oct. 17, 2013, now Pat. No. 9,551,697.

(51) Int. Cl.
  *G01N 27/447* (2006.01)
  *G01N 27/22* (2006.01)
  *G01N 33/487* (2006.01)

(52) U.S. Cl.
  CPC ... *G01N 27/44791* (2013.01); *G01N 27/4473* (2013.01); *G01N 27/44743* (2013.01); *G01N 33/48721* (2013.01)

(58) Field of Classification Search
  CPC ....... G01N 27/447–27/44795; G01N 27/3278; G01N 33/48721

(Continued)

(56) References Cited

U.S. PATENT DOCUMENTS

| 5,235,267 A | 8/1993 | Schoneberg |
| 5,541,851 A | 7/1996 | Sato |

(Continued)

FOREIGN PATENT DOCUMENTS

| EP | 1712891 | 10/2006 |
| JP | 2004333485 | 11/2004 |

(Continued)

OTHER PUBLICATIONS

Schuster et al., Self-Assembled α-Hemolysin Pores in an S-Layer-Supported Lipid Bilayer, Biochimica et Biophysica Acta 1370, (1998) 280-288.

(Continued)

*Primary Examiner* — Bach T Dinh
(74) *Attorney, Agent, or Firm* — Van Pelt, Yi & James LLP

(57) ABSTRACT

A method of identifying a molecule is disclosed. A molecule is drawn to a nanopore by applying a first voltage signal to a pair of electrodes during a first period, wherein the first voltage signal causes a first ionic current through the nanopore that is indicative of a property of a portion of the molecule proximate to the nanopore. The molecule is released from the nanopore by applying a second voltage signal to the pair of electrodes during a second period, wherein the second voltage signal causes a second ionic current through the nanopore. The first period and the second period are determined based at least in part on a net ionic current through the nanopore comprising the first ionic current and the second ionic current.

23 Claims, 20 Drawing Sheets

(58) Field of Classification Search
USPC ............... 204/450–470, 546–550, 600–621, 204/643–645; 435/6.11, 6.12
See application file for complete search history.

(56) References Cited

U.S. PATENT DOCUMENTS

| | | | |
|---|---|---|---|
| 5,747,805 | A | 5/1998 | Youngquist |
| 7,468,271 | B2 | 12/2008 | Golovchenko et al. |
| 7,572,624 | B2 | 8/2009 | Gumbrecht |
| 9,551,697 | B2 * | 1/2017 | Chen ................ C01N 33/48721 |
| 9,605,307 | B2 | 3/2017 | Chen |
| 9,869,655 | B2 | 1/2018 | Chen |
| 2003/0102263 | A1 | 6/2003 | Lopez |
| 2004/0053337 | A1 | 3/2004 | Yamazaki |
| 2004/0262636 | A1 | 12/2004 | Yang |
| 2005/0239134 | A1 | 10/2005 | Gorenstein |
| 2006/0105373 | A1 | 5/2006 | Pourmand |
| 2006/0246497 | A1 | 11/2006 | Huang |
| 2008/0094076 | A1 | 4/2008 | Hibbs |
| 2010/0078325 | A1 | 4/2010 | Oliver |
| 2011/0168551 | A1 | 7/2011 | White |
| 2012/0133354 | A1 | 5/2012 | Canas |

FOREIGN PATENT DOCUMENTS

| | | |
|---|---|---|
| JP | 2005538377 | 12/2005 |
| JP | 2008507703 | 3/2008 |
| JP | 2010502936 | 1/2010 |
| WO | WO-03095617 | 11/2003 |
| WO | WO-2007115694 | 10/2007 |
| WO | WO-2008079169 | 7/2008 |
| WO | WO-2009005547 | 1/2009 |
| WO | WO-2009047703 | 4/2009 |
| WO | WO-2009077734 | 6/2009 |
| WO | WO-2009138760 | 11/2009 |
| WO | WO-2010044932 | 4/2010 |
| WO | WO-2013011879 | 1/2013 |

OTHER PUBLICATIONS

Thei et al., Parallel Recording of Single Ion Channels: A Heterogeneous System Approach, IEEE Transactions on Nanotechnology, vol. 9, No. 3, May 2010.
Nakane et al., Nanopore Sensors for Nucleic Acid Analysis, Journal of Physics, Condensed Matter 15.32, Aug. 1, 2003, R1365.
Chen et al., Probing Single DNA Molecule Transport using Fabricated Nanopores, (Nano Lett, 2004, 4(11), pp. 2293-2298).

* cited by examiner

```
* WE=Electroplated Pd, 24uL, 500mM KAc, 10mM KCl, CE=AgCl Can
* bilayerpop_gentle, getpore_acetate2 (deactivation at 15pA)
* 011_
JP_P24_1165_SCW2R12C24_130212_Exp0073l
V0 1 0 PULSE(0 0.2 0 500us 500us 99.5ms 200ms)
C0 2 1 300e12
R0 3 2 100e6
* C2 3 0 100e15
S1 3 4 3 0 switch1 ON
.model switch1 sw vt=0 vh=0 ron=1e3 roff=1e12
B1 4 0 I = 0.3 * ( 8.829e10*
v(4)^2 + 8.9292e10*
v(4))
S2 3 5 0 3 switch2 ON
.model switch2 sw vt=0 vh=0 ron=1e3 roff=1e12
B2 5 0 I = 0.3 * ( 1.2232e9*
v(5)^2 + 8.3668e10*
v(5))
.END
.tran 50us 27s
```

FIG. 11

NON-FARADAIC, CAPACITIVELY COUPLED MEASUREMENT IN A NANOPORE CELL ARRAY

CROSS REFERENCE TO OTHER APPLICATIONS

This application is a continuation of co-pending U.S. patent application Ser. No. 14/056,795 entitled NON-FARADAIC, CAPACITIVELY COUPLED MEASUREMENT IN A NANOPORE CELL ARRAY filed Oct. 17, 2013 which is incorporated herein by reference for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. It would be desirable to develop techniques for biochips that make them more robust, efficient, and cost-effective.

BRIEF DESCRIPTION OF THE DRAWINGS

Various embodiments of the invention are disclosed in the following detailed description and the accompanying drawings.

FIG. 11 illustrates an embodiment of a simulation model that was matched to the data of FIG. 10.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size. When a molecule, such as a DNA or RNA molecule, partially or completely blocks the nanopore, the magnitude of the current through the nanopore changes. It has been shown that the ionic current blockade can be correlated with the base pair sequence of the DNA or RNA molecule.

A nanopore based sequencing chip may be used for DNA sequencing. A nanopore based sequencing chip incorporates a large number of autonomously operating sensor cells configured as an array. For example, an array of one million cells may include 1000 rows by 1000 columns of cells.

Figure 1:
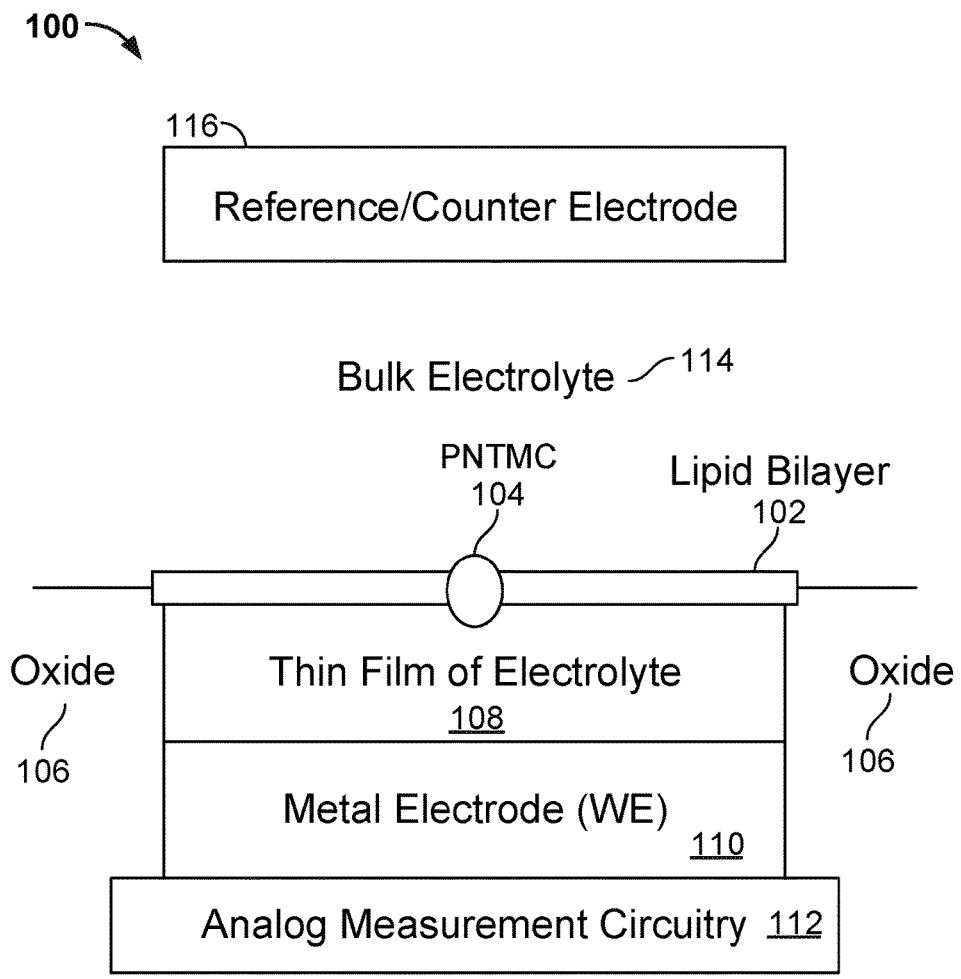
FIG. 1 illustrates an embodiment of a cell in a nanopore based sequencing chip. A lipid bilayer 102 is formed over the surface of the cell.

FIG. 1 illustrates an embodiment of a cell in a nanopore based sequencing chip. A lipid bilayer 102 is formed over the surface of the cell. The bulk electrolyte 114 containing soluble protein nanopore transmembrane molecular complexes (PNTMC) and the analyte of interest is placed directly onto the surface of the cell. A single PNTMC 104 is inserted into lipid bilayer 102 by electroporation. The individual lipid bilayers in the array are not connected to each other either chemically or electrically. Thus, each cell in the array is an independent sequencing machine, producing data unique to the single polymer molecule associated with the PNTMC. PNTMC 104 operates on the analytes and modulates the ionic current through the otherwise impermeable bilayer. The ionic current is read by analog measurement circuit 112 in each cell, converted to digital information and transmitted out of the cell. In some embodiments, the transmission data rate is on the order of gigabits per second. In some embodiments, a field programmable gate array (FPGA) or application-specific integrated circuit (ASIC) receives the transmitted data, processes the data, and forwards the data to a computer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable lipid bilayer 102. PNTMC 104 crosses lipid bilayer 102 and provides the only path for ionic current to flow from the bulk liquid to metal electrode 110. Metal electrode 110 is also referred to as the working electrode (WE). The cell also includes a counter/reference electrode (CE/RE) 116, which is an electrochemical potential sensor.

Figure 2:
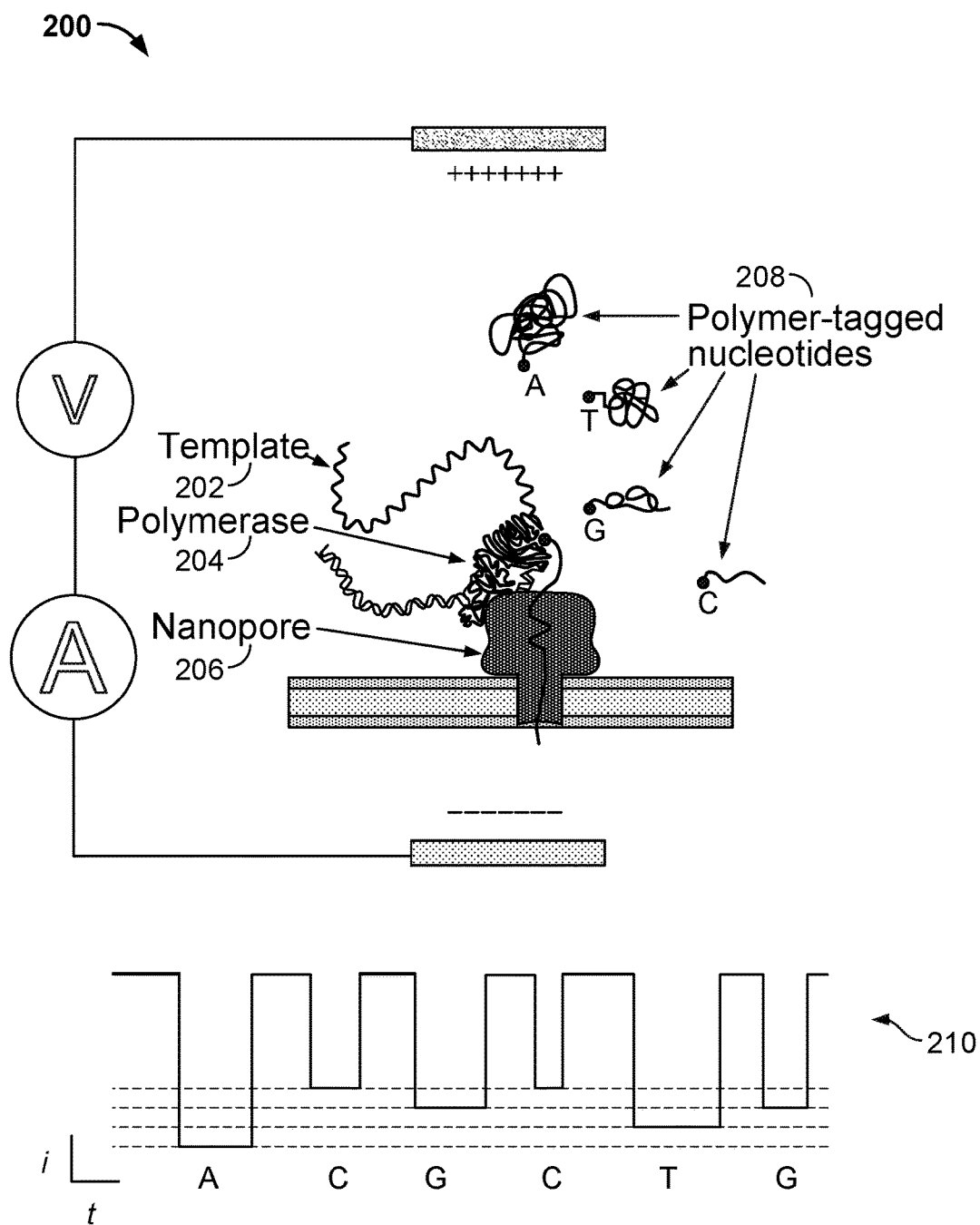
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the vestibule of nanopore 206. The tails of the tags can be modified to have strong affinity with the amino acid residues in the vestibule of nanopore 206. After polymerase catalyzed incorporation of the correct nucleotide, the tag-attached polyphosphate is released and passes through nanopore 206 to generate a unique ionic current blockade signal 210, thereby identifying the added base electronically due to the tags' distinct chemical structures.

Figure 3:
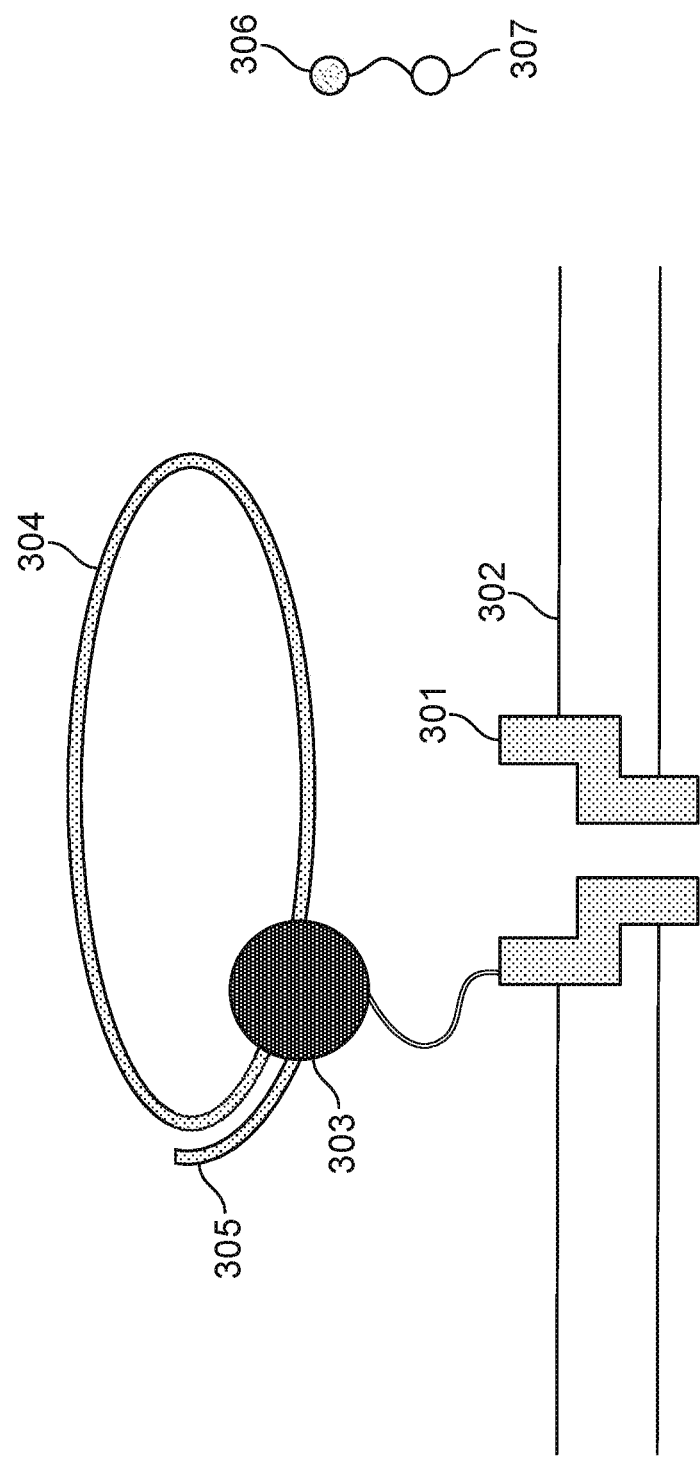
FIG. 3 illustrates an embodiment of a cell performing nucleotide sequencing with pre-loaded tags.

FIG. 3 illustrates an embodiment of a cell performing nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a single stranded nucleic acid molecule 304 to be sequenced. In some embodiments, single stranded nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
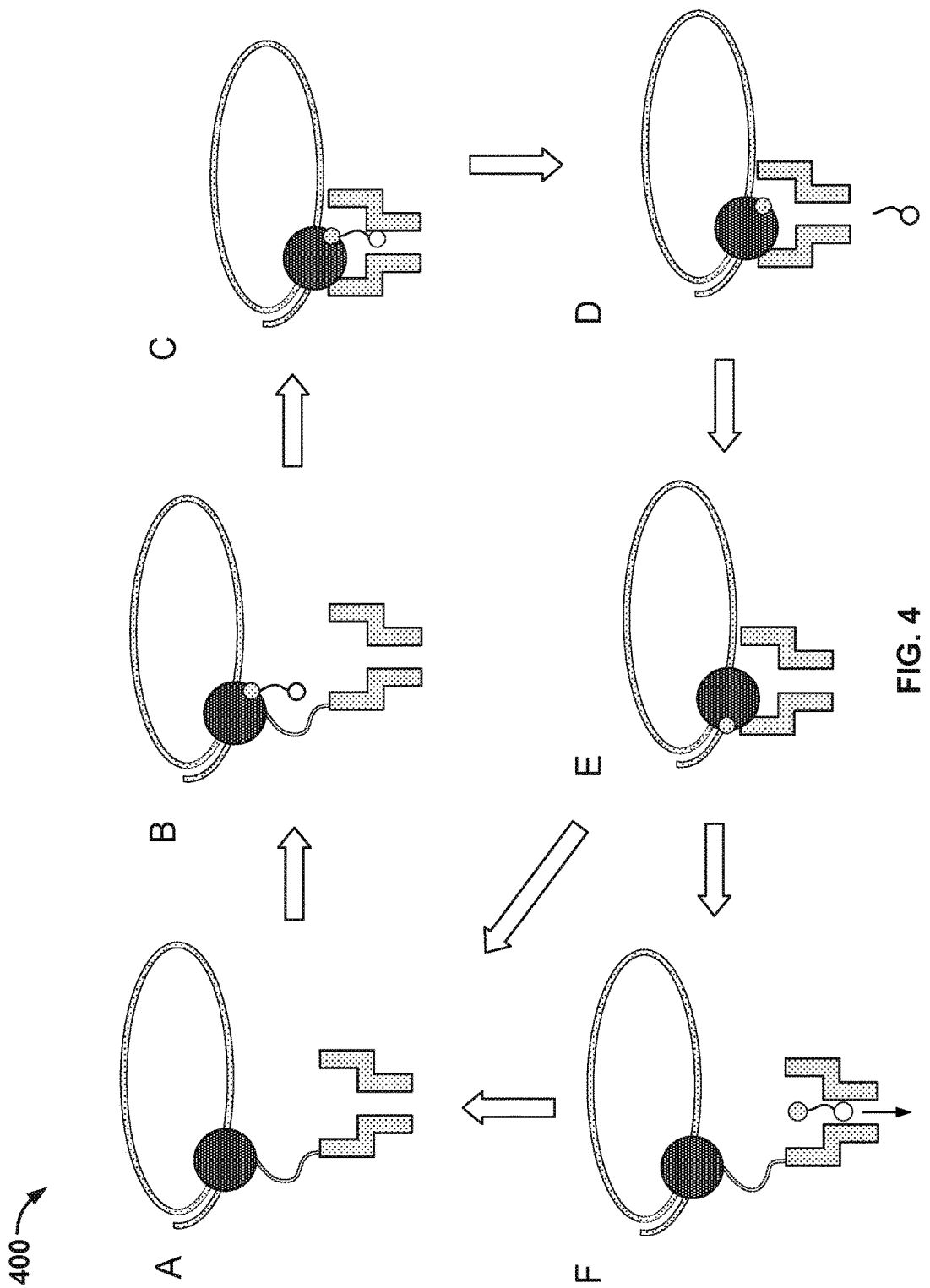
FIG. 4 illustrates an embodiment of a process 400 for nucleic acid sequencing with "pre-loaded" tags.

FIG. 4 illustrates an embodiment of a process 400 for nucleic acid sequencing with "pre-loaded" tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 1000 ms. In some cases, a tag that is "pre-loaded" is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. A voltage (e.g., a DC or AC voltage) may be applied to the nanopore or the membrane in which the nanopore resides to draw the polymerase to the nanopore. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are base paired with the single stranded nucleic acid molecule (e.g., A with T and G with C). However, some of the associated tagged nucleotides are not base paired with the single stranded nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the current passing through the nanopore is ~30 picoamps (pA). At stage C, the current flowing through the nanopore is about 6 pA, 8 pA, 10 pA, or 12 pA, each amperage corresponding to one of the four types of tagged nucleotides. The polymerase undergoes an isomerization and a transphosphorylation reaction to incorporate the nucleotide into the growing nucleic acid molecule and release the tag molecule. At stage D, the released tag passes through the nanopore. The tag is detected by the nanopore. In particular, as the tag passes through the nanopore, a unique ionic current blockade signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule.

In some cases, tagged nucleotides that are not incorporated into the growing nucleic acid molecule will also pass through the nanopore, as seen in stage F of FIG. 4. The un-incorporated nucleotide can be detected by the nanopore in some instances, but the method provides a means for distinguishing between an incorporated nucleotide and an un-incorporated nucleotide based at least in part on the time for which the nucleotide is detected in the nanopore. Tags bound to un-incorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Two types of ionic flow can be driven through the PNTMC—faradaic conduction and non-faradaic conduction. In faradaic conduction, a chemical reaction occurs at the surface of the metal electrode. The faradaic current is the current generated by the reduction or oxidation of some chemical substances at an electrode. In non-faradaic conduction, no chemical reaction happens at the surface of the metal. The changing potential on the double layer capacitance between the metal electrode and the thin film of electrolyte drives the ion flow.

Ionic flow by faradaic conduction has a number of drawbacks. The operational lifespan of an electrode is limited because the metal in the electrode is consumed and depleted as the ionic current flows through the PNTMC, as will be described in greater detail below.

Figure 5:
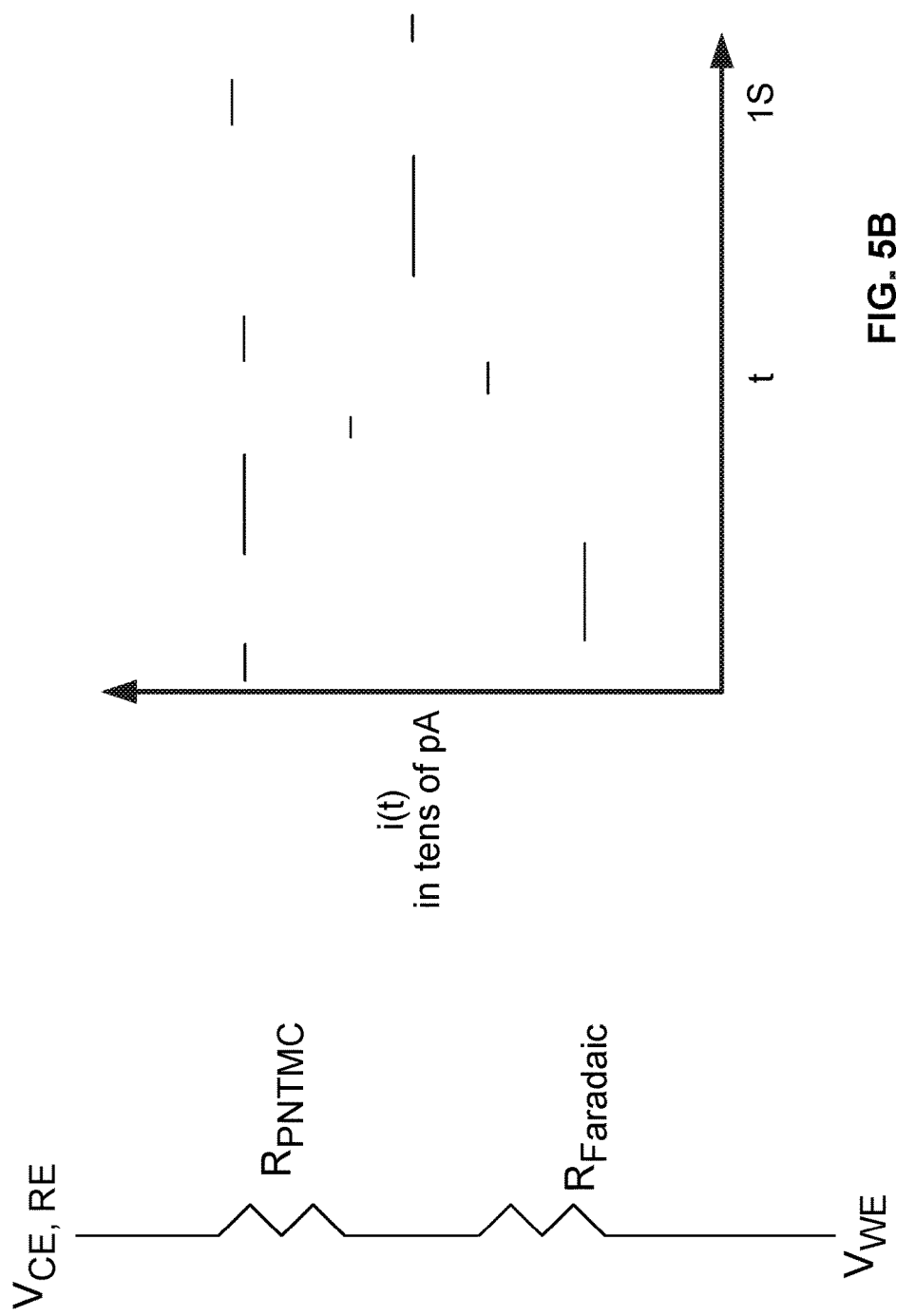
FIG. 5A illustrates an embodiment of a small signal circuit model during faradaic conduction.
FIG. 5B illustrates the different states of the PNTMC with faradaic conduction.

FIG. 5A illustrates an embodiment of a small signal circuit model during faradaic conduction. The PNTMC and WE are represented as simple resistors in the small signal circuit model. FIG. 5B illustrates the different states of the PNTMC with faradaic conduction. The ionic current flow, i(t), has five states: the highest current state with an open nanopore channel (not shown) and four lower current states corresponding to each of four different types of nucleotides bound to the active site of the PNTMC. Positive current flow i(t) describes electrons entering the $V_{CE, RE}$ node and leaving the $V_{WE}$ node. Anions (e.g., Cl⁻) leave the CE, flow through the bulk electrolyte, cross the lipid bilayer via the PNTMC, and continue through the thin film of electrolyte and combine with the metal of the WE.

For example, for an electrode with silver metal (Ag), the chemical reaction is:

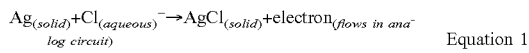

$$Ag_{(solid)} + Cl^-_{(aqueous)} \rightarrow AgCl_{(solid)} + electron_{(flows\ in\ analog\ circuit)} \quad \text{Equation 1}$$

As shown in Equation 1 above, an atom of metallic silver is converted to an insoluble salt, silver-chloride (AgCl), for each chloride anion (Cl⁻) that passes through the PNTMC. In some cases, the silver is depleted within minutes of operation.

To avoid depletion of the metal electrode, the direction of the ionic current flow may be reversed by applying a negative voltage for a similar duration, causing the silver-chloride (AgCl) to be converted back to silver metal. However, recharging or refreshing in this manner causes the silver to be re-deposited as hair-like features on the surface of the metal electrode, which may impact overall performance, especially in chips with smaller cell geometry and thus smaller electrodes.

Another way is to delay the depletion of the metal electrode by applying a voltage to draw the polymerase to the nanopore and pull the tag through or to the proximity of the nanopore for detection, and then turn off the voltage for a period of time, which will cause the tag to be released from the nanopore. Since there is no current while the voltage is turned off, fewer silver atoms are converted and the lifespan of the metal electrode is prolonged. However, the detection time is reduced accordingly.

In addition to depletion of the metal electrode, faradaic conduction also causes an imbalance in the concentration of the bulk electrolyte within the cells over time. For example, there is a net gain of KCl molecules at one electrode but a net loss of KCl molecules at the opposite electrode. This salt concentration buildup at one electrode and salt depletion on the opposite electrode creates undesirable osmotic pressure within the cell.

An alternative type of ionic flow through the PNTMC is via non-faradaic conduction. In non-faradaic conduction, no chemical reaction (reduction or oxidation of chemical substances) occurs at the surface of the metal. The changing potential across the double layer capacitance between the metal electrode and the thin film of electrolyte drives the ion flow.

For non-faradaic conduction, the metal electrode may be made of metals that are resistant to corrosion and oxidation. For example, noble metals such as platinum or gold oxidize with difficulty, and even when they do oxidize, the process is easily reversible. When small potentials (e.g., less than +/−1 V relative to $V_{CE}$) are applied to platinum/gold in an electrolyte, aside from an initial capacitive transient, no ionic current flows. This allows the measurement of electron tunneling from the metal into redox (reduction-oxidation) active species mixed into the electrolyte. Without redox active species (such as Ferricyanide or Ferrocyanide) in the electrolyte, no steady state ionic (or electron or hole) current flows across the metal-liquid interface. Despite the lack of chemical (i.e., bonding) interaction between the platinum/gold and the electrolyte, there is transient physical displacement of ions in the electrolyte from the growth and shrinkage of the ion depletion region at the metal-liquid interface, in response to the applied potential. This ion depletion region is referred to as a "double layer" in electrochemistry parlance. Using an electrical engineering model, a parallel plate capacitor forms where the metal is one plate, the depletion region is the dielectric, and the diffuse distribution of ions in the liquid is the other plate.

Figure 6:
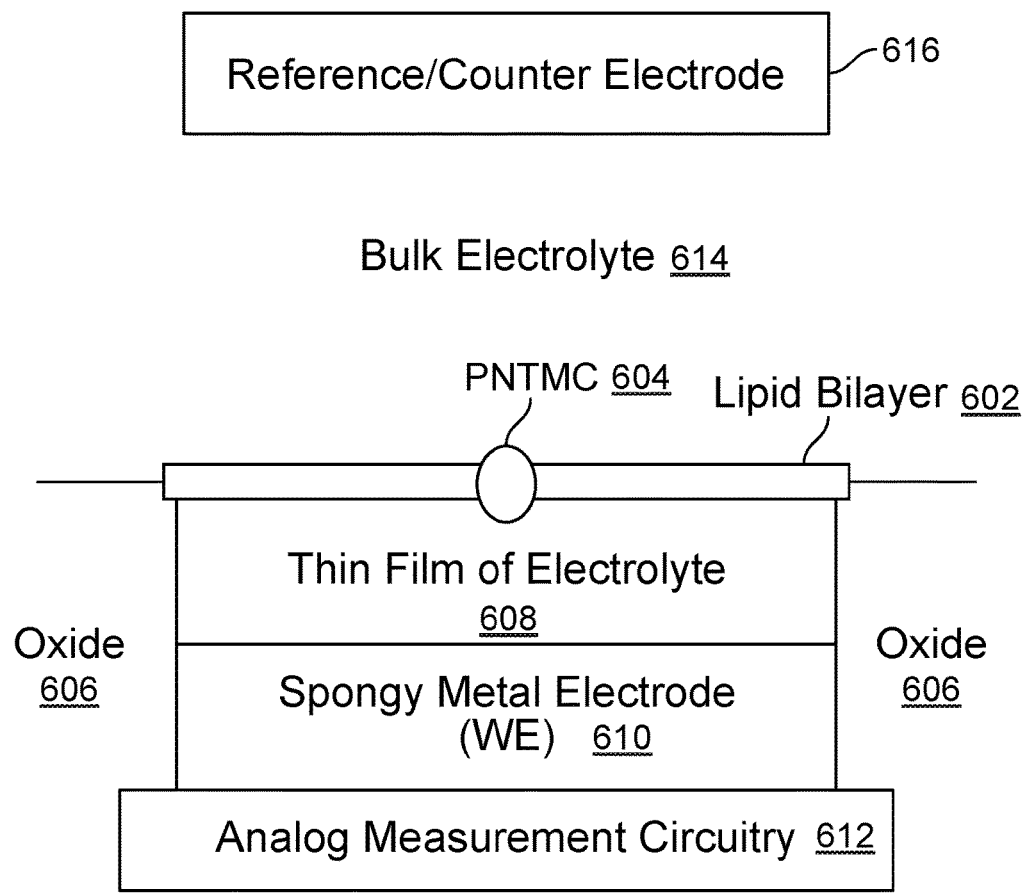
FIG. 6 illustrates an embodiment of a cell in a nanopore based sequencing chip configured for non-faradaic and capacitively coupled measurements.

FIG. 6 illustrates an embodiment of a cell in a nanopore based sequencing chip configured for non-faradaic and capacitively coupled measurements. A lipid bilayer 602 is formed over the surface of the cell. The electrolyte containing soluble protein nanopore transmembrane molecular complexes (PNTMC) and analyte of interest 614 is placed directly onto the surface of the cell. A single PNTMC 604 is inserted into lipid bilayer 602 by electroporation. The individual lipid bilayers in the array are not connected to each other either chemically or electrically. Thus, each cell in the array is an independent sequencing machine producing data unique to the single polymer molecule associated with the PNTMC. The cell includes an analog measurement circuit 612 for making non-faradaic and capacitively coupled measurements. The measurements are converted to digital information and transmitted out of the cell. In some embodiments, the transmission data rate is on the order of gigabits per second. In some embodiments, a field programmable gate array (FPGA) or an application-specific integrated circuit (ASIC) receives the transmitted data, processes the data, and forwards the data to a computer.

With continued reference to FIG. 6, analog measurement circuitry 612 is connected to a metal electrode 610 covered by a thin film of electrolyte 608. The thin film of electrolyte 608 is isolated from the bulk electrolyte 614 by the ion-impermeable lipid bilayer 602. PNTMC 604 crosses lipid bilayer 602 and provides the only path for ionic flow from the bulk liquid to metal electrode 610. Metal electrode 610 is also referred to as the working electrode (WE). For non-faradaic conduction, metal electrode 610 may be made of metals that are resistant to corrosion and oxidation, e.g., platinum, gold, and graphite. Metal electrode 610 may be a spongy electrode, as will be described in greater detail below. The cell also includes a counter/reference electrode (CE/RE) 616, which is an electrochemical potential sensor.

Figure 7:
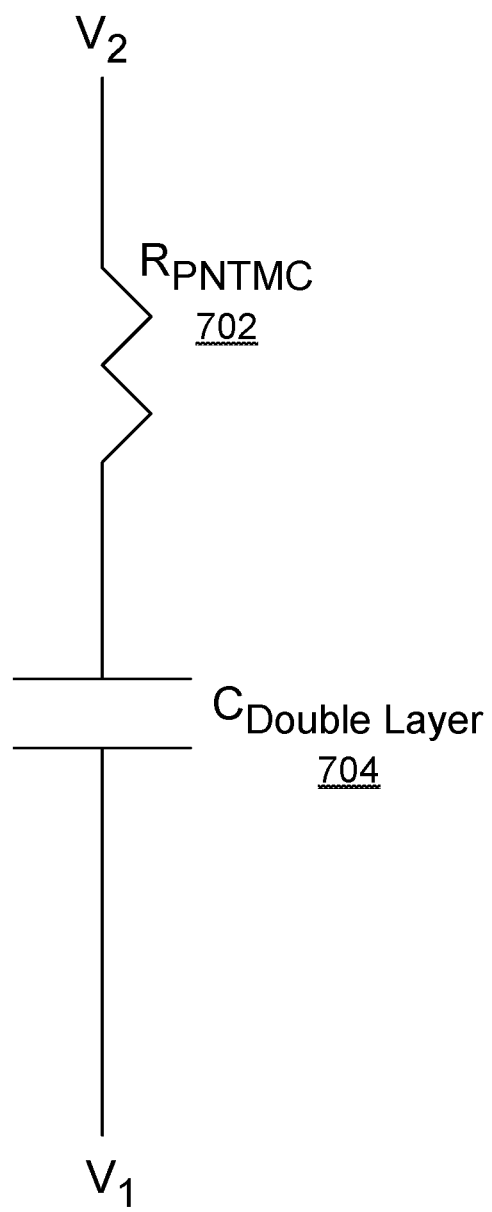
FIG. 7 illustrates an embodiment of a small signal circuit model for non-faradaic conduction.

FIG. 7 illustrates an embodiment of a small signal circuit model for non-faradaic conduction. The PNTMC is represented as a simple resistor 702 in the small signal circuit model. The double layer capacitance is represented as a capacitor 704 in the small signal circuit model. In some embodiments, $V_1$ in FIG. 7 is set to be an incremental voltage from ground, e.g., 500 mV, while $V_2$ is set to be $V_1$ plus an applied signal, e.g., an applied AC signal from 10 Hz to 1 kHz.

In some embodiments, the applied signal is an AC signal. At one polarity, the applied AC signal draws the polymerase to the nanopore and draws the tag through or to the proximity of the nanopore for detection. When the polarity of the applied AC signal is reversed, the tag is released from the nanopore, and the electrode is recharged/refreshed such that no electrochemical changes are made to the metal electrodes. As the AC signal repeatedly changes polarity, a portion of a tag associated with a tagged nucleotide is directed into a nanopore and directed out of the nanopore for a plurality of times. This repetitive loading and expulsion of a single tag allows the tag to be read multiple times. Multiple reads may enable correction for errors, such as errors associated with tags threading into and/or out of a nanopore.

In some embodiments, the frequency of the AC signal is chosen at least in part based on the time period during which a tagged nucleotide is associated with a polymerase. The frequency of the AC signal should allow a tagged nucleotide associated with the polymerase to be drawn and loaded into the nanopore for a sufficient length of time at least once such that the tag can be detected; otherwise, some of the tags that are associated with the polymerase cannot be detected by the system. In other words, the sampling should be at a rate faster than the rate at which the sequence of events is occurring, such that no events are missed.

Figure 8A:
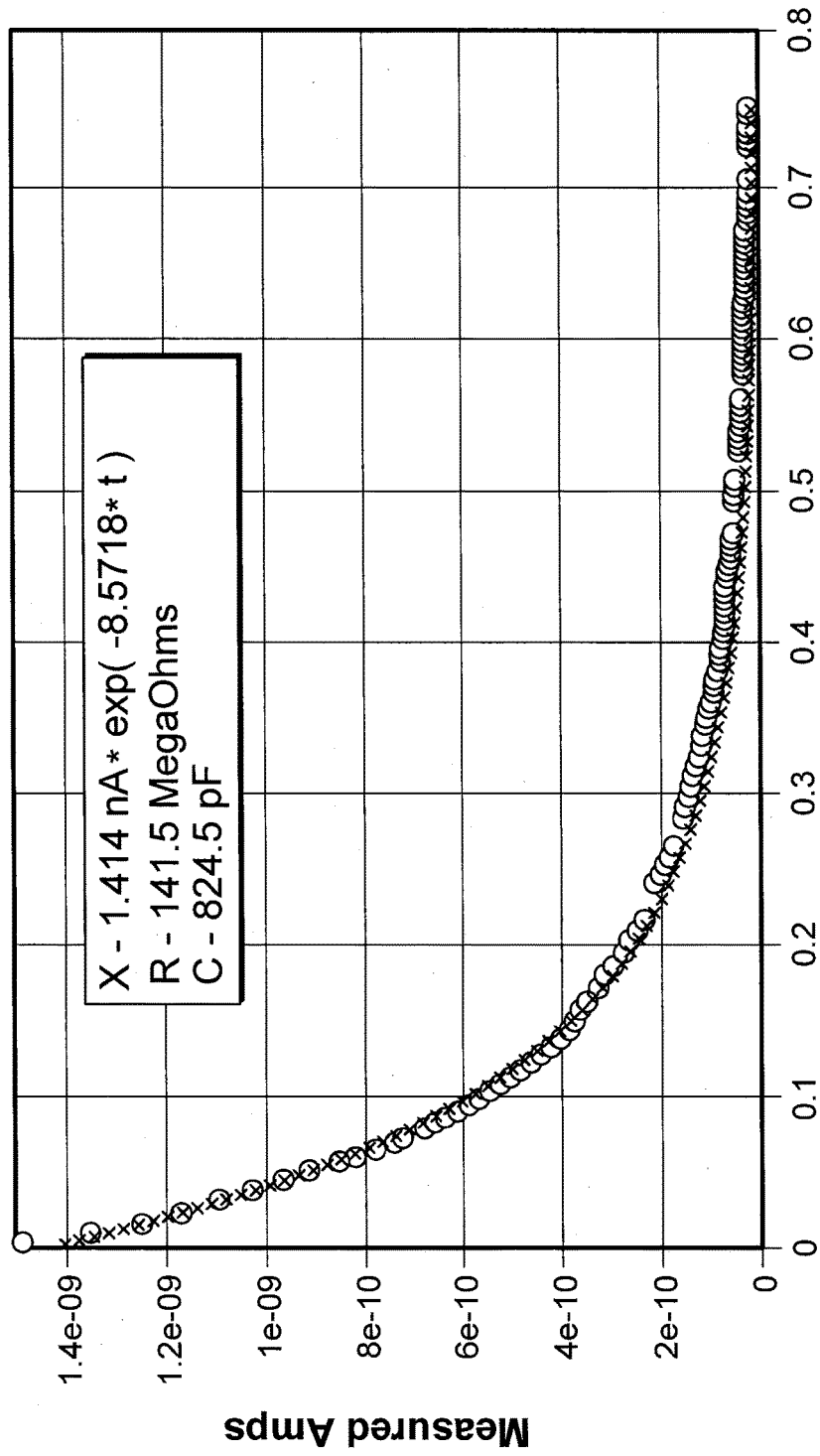
FIG. 8A and FIG. 8B illustrate an embodiment of the capacitive response of the double layer.
Figure 8B:
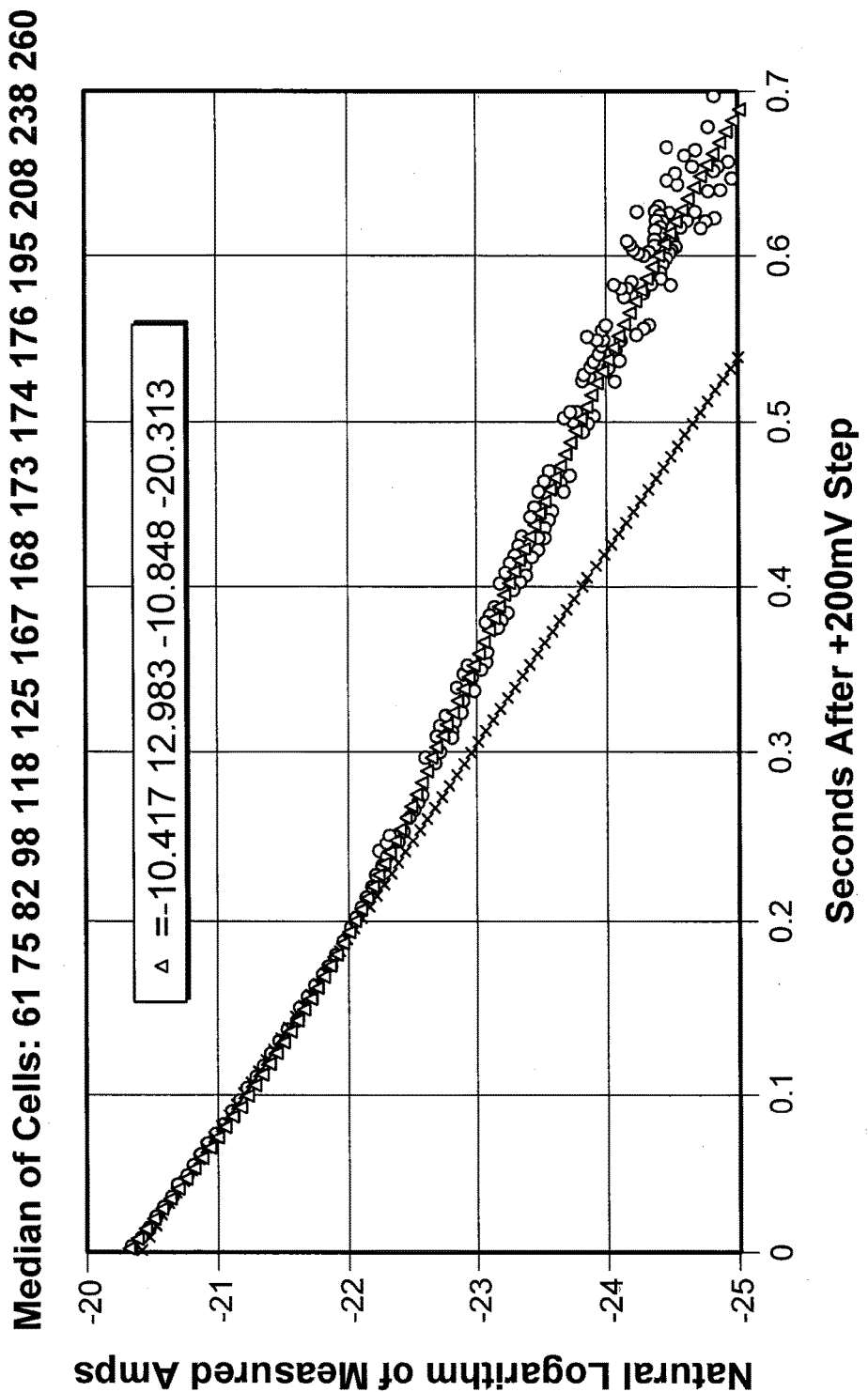

With continued reference to FIG. 6, before the lipid bilayer 602 has been formed, the bulk electrolyte 614 is in direct contact with the working electrode 610, thus creating a short circuit between the electrolyte and the working electrode. FIG. 8A and FIG. 8B illustrate an embodiment of the capacitive response of the double layer. The figures illustrate the properties of the double layer with a short circuit between the electrolyte and the working electrode. In this example, the electrolyte contains 0.5 M Potassium Acetate and 10 mM KCl. The counter electrode 616 includes AgCl. The working electrode 610 is a platinum electrode with electroplated platinum. Water viscosity prevents the easy flow of ions in response to the applied field; this is manifested as a series resistance in the double layer capacitive response. This resistance limits the peak current as shown in FIG. 8A. The series nature of the RC electrochemical connection can be seen in the decay of the response, which is characterized by the RC time constant. In FIG. 8B, the current is shown to fall to exp (−25)=13.8 pA, below the detection limit of the system. This demonstrates a lack of both shunt resistance (from an electrical point of view) and faradaic current (from an electrochemical point of view).

The working electrode 610 is configured to maximize its surface area for a given volume. As the surface area increases, the capacitance of the double layer increases, and a greater amount of ions can be displaced with the same applied potential before the capacitor becomes charged. Referring to FIG. 7, the impedance of $$C_{Double\ Layer} = \frac{1}{(j*2*pi*f*c)},$$

where f=frequency and C=$C_{Double\ Layer}$. By making f, C, or both f and C larger, the capacitor's impedance becomes very small relative to $R_{PNTMC}$, and the current to be measured becomes larger. As the impedance of the small signal model is dominated by $R_{PNTMC}$, the measured current can better differentiate the five states: the highest current state with an open nanopore channel and four lower current states corresponding to each of four different types of nucleotides bound into the active site of the PNTMC.

For example, the surface area of the working electrode may be increased by making the electrode "spongy." In some embodiments, the capacitance of the double layer to the bulk liquid can be enhanced by electroplating platinum metal onto a 5 micron diameter smooth platinum electrode in the presence of a detergent. The detergent creates nanoscale interstitial spaces in the platinum metal, making it "spongy." The platinum sponge soaks up electrolyte and creates a large effective surface area (e.g., 33 pF per square micron of electrode top-down area). Maximizing the double layer surface area creates a "DC block" capacitor, whereby the voltage on the double layer reaches steady state and barely changes during operation. The series PNTMC resistance ($R_{PNTMC}$ in FIG. 7) and the double layer capacitance ($C_{Double\ Layer}$ in FIG. 7) form a low frequency zero, which acts as a high pass filter. In one example, $R_{PNTMC}$~10 gigaohm, $C_{Double\ Layer}$ ~800 pF, resulting in a time constant of ~10 gigaohm*~800 pF=~8 second time constant. Chopping the measurement at 100 Hz then rejects DC drift and attenuates low frequency information content in the measured tags by a factor of 1000.

Without any tags present, the PNTMC behaves similar to an alpha hemolysin protein nanopore. The hemolysin nanopore has a rectifying characteristic which changes its bias depending on the duty cycle of the square wave drive. Unlike the faradaic conduction case, the absolute voltage applied to the electrode is not the same as the voltage applied to the nanopore: the voltage on the double layer biases the potential applied to the nanopore, and this bias changes with the duty cycle.

Figure 9A:
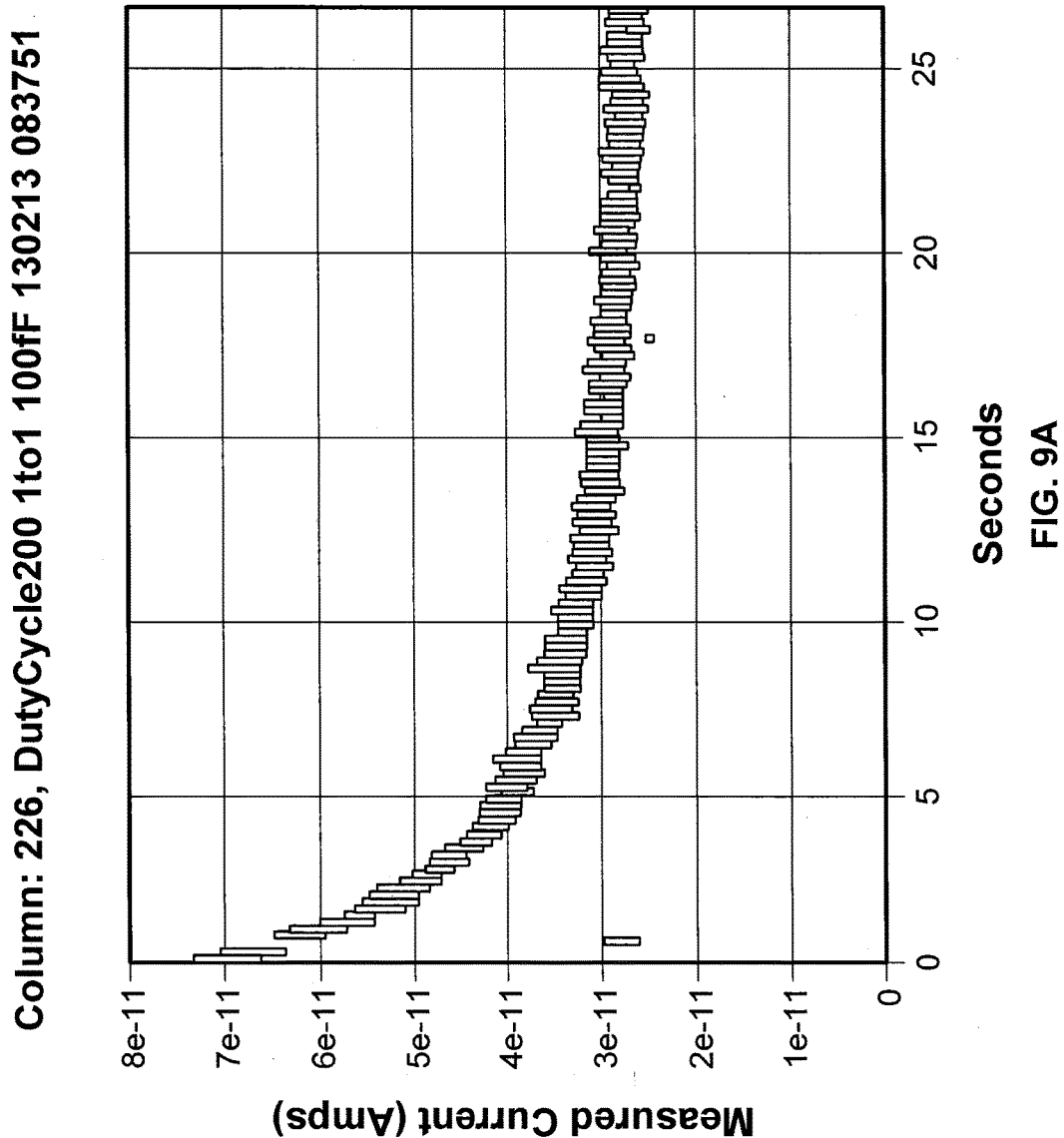
FIG. 9A shows the startup transient when 200 mV with positive polarity is applied to the nanopore.
Figure 9B:
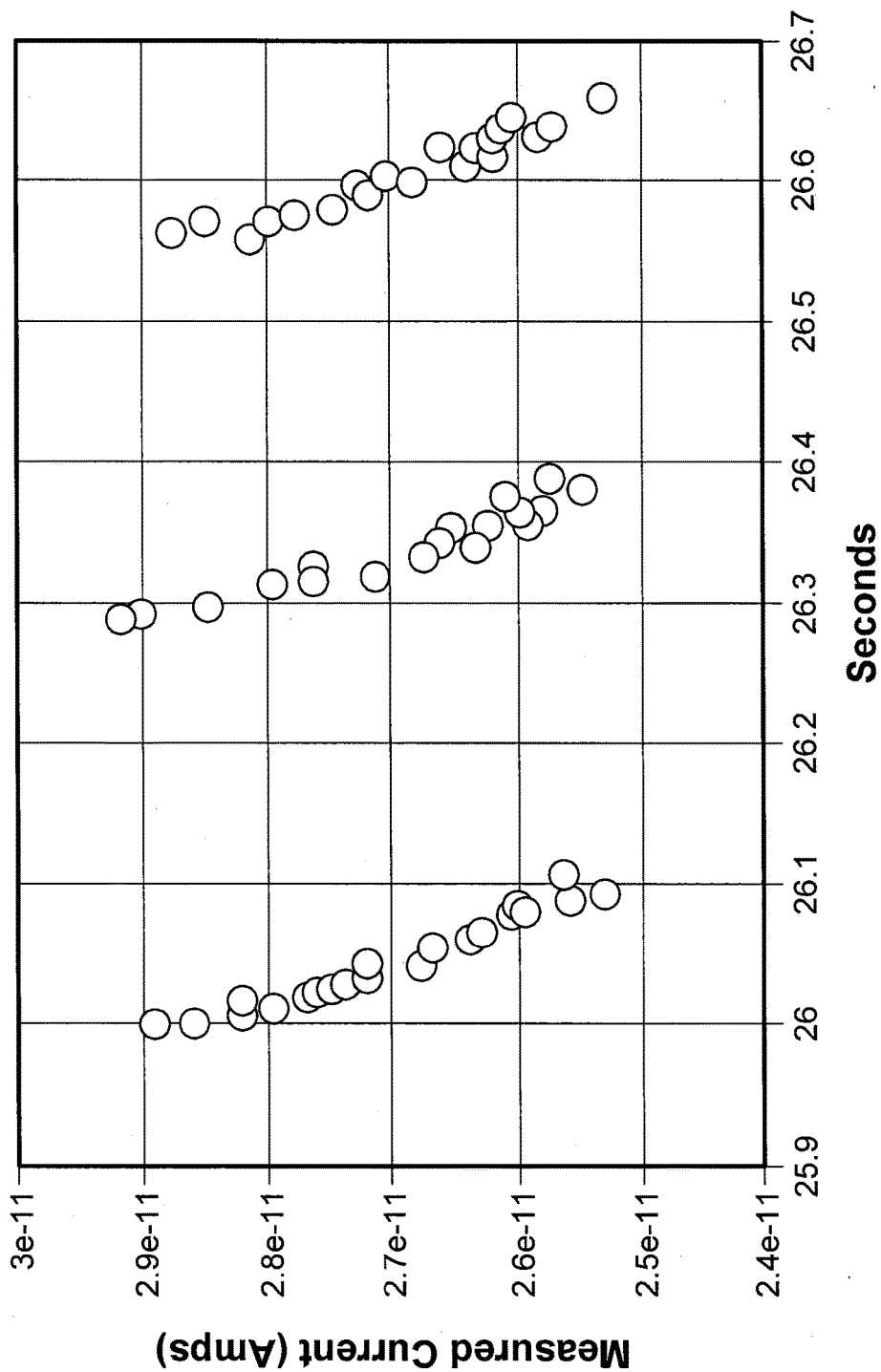
FIG. 9B illustrates the decay rate of the voltage on the double layer capacitor.

FIGS. 9A and 9B illustrate the nanopore current with non-faradaic AC modulation. In this example, the applied signal is a 200 mV peak to peak square wave with a 50% duty cycle at 5 Hz. The electrolyte contains 0.5 M Potassium Acetate and 10 mM KCl. The counter electrode 616 includes AgCl. The working electrode 610 is a platinum electrode with electroplated platinum.

FIG. 9A shows the startup transient when 200 mV with positive polarity is applied to the nanopore, indicating that the open channel current with 200 mV directly applied is approximately 70 pA. FIG. 9A shows that the steady state is reached after ~20 seconds. In FIG. 9B, the decay rate of the voltage on the double layer capacitor can be observed. The decay rate is determined by the size of the double layer capacitance and the nanopore load resistance.

Figure 10:
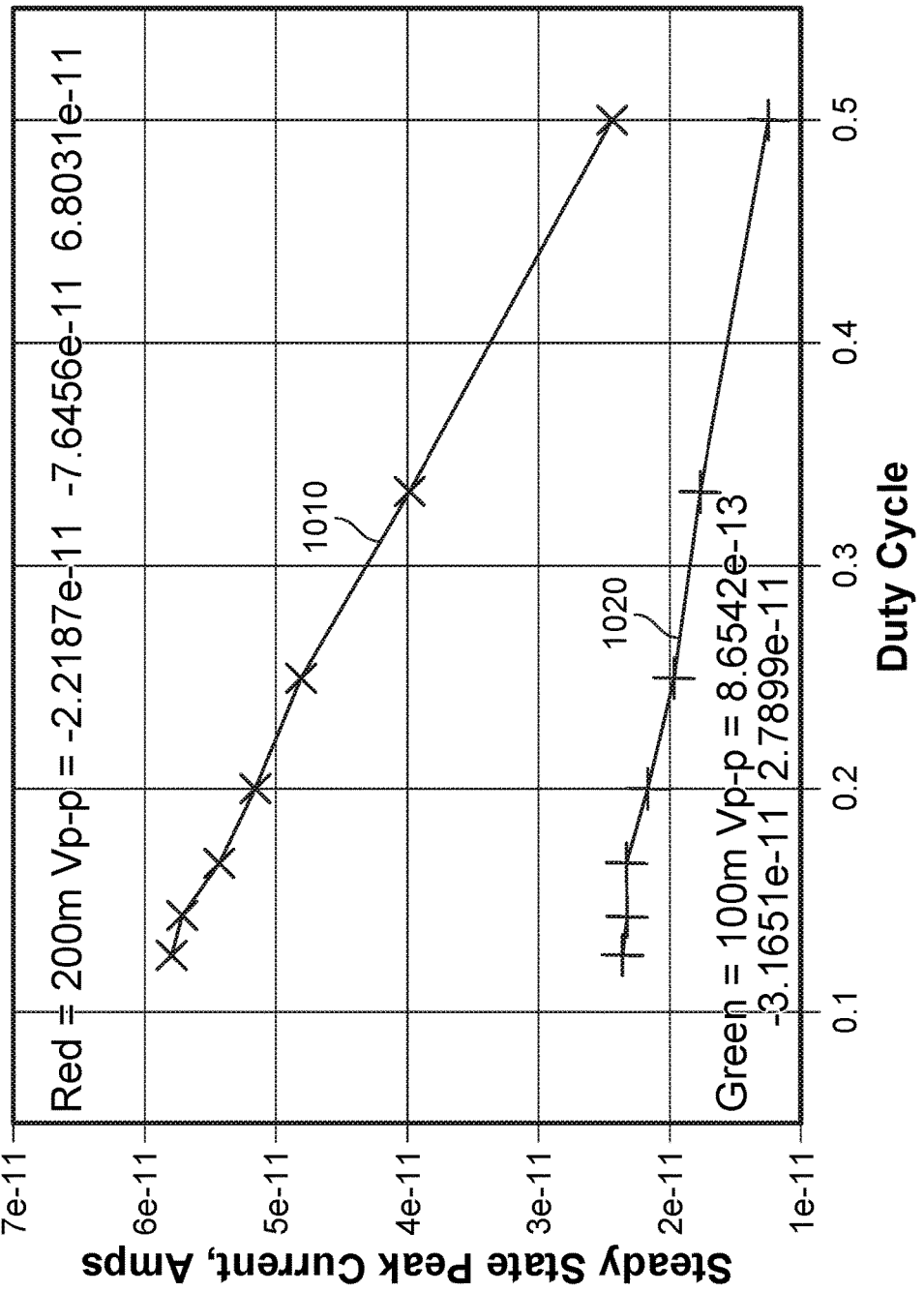
FIG. 10 illustrates that the peak positive current at steady state varies as a function of duty cycle and applied voltage.

FIG. 10 illustrates that the peak positive current at steady state varies as a function of duty cycle and applied voltage. Plot 1010 shows the steady state peak current in amperes (A) plotted against different duty cycles when the applied voltage is a 200 mV peak to peak square wave. Plot 1020 shows the steady state peak current (in A) plotted against different duty cycles when the applied voltage is a 100 mV peak to peak square wave. In this example, the electrolyte contains 0.5 M Potassium Acetate and 10 mM KCl. The counter electrode 616 includes AgCl. The working electrode 610 is a platinum electrode with electroplated platinum. Since the hemolysin nanopore has a rectifying characteristic (or is non-ohmic), a larger magnitude negative polarity voltage is required to pass the same magnitude of current than when a positive polarity voltage is applied. The peak positive current drops as the duty cycle is increased. The lower the duty cycle, the higher the positive voltage applied to the nanopore through the double layer capacitance.

Figure 12A:
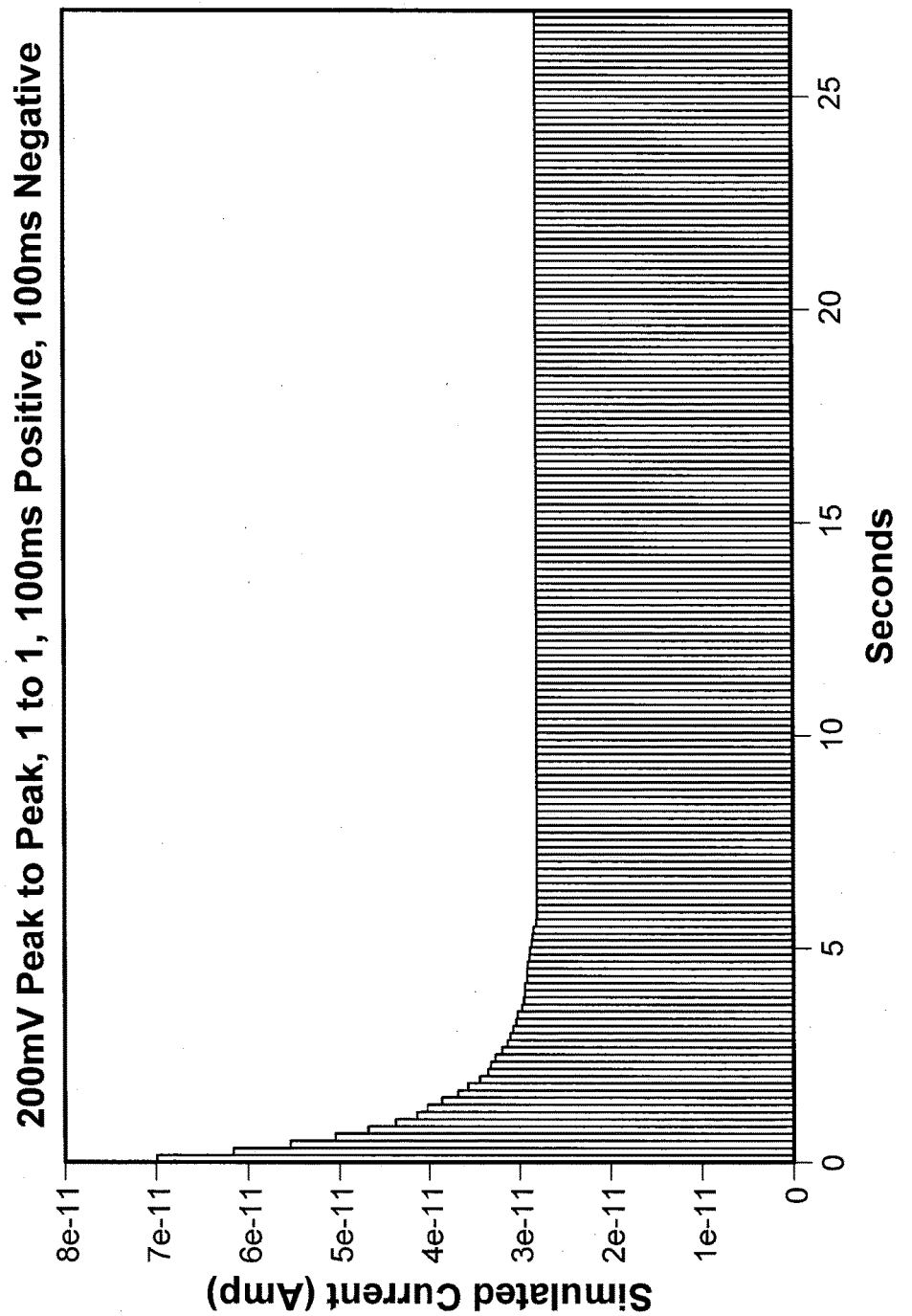
FIGS. 12A and 12B illustrate the simulation result when the applied signal has a 50% duty cycle.
Figure 12B:
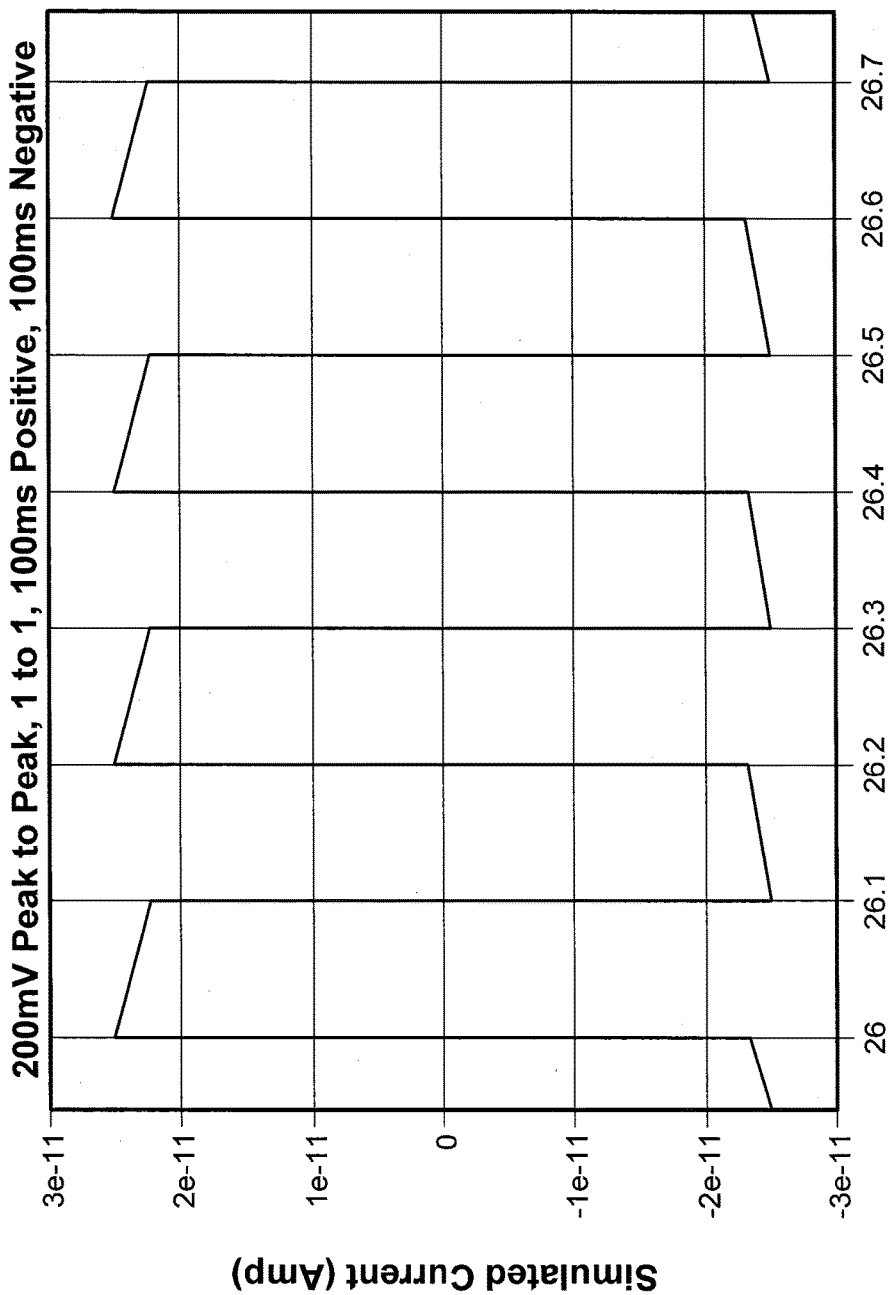

FIG. 11 illustrates an embodiment of a simulation model that was matched to the data of FIG. 10. The simulation is constructed to estimate the actual voltage on the nanopore, which is not the same as the voltage applied to the working electrode because of the double layer capacitor connected in series with the nanopore. This voltage cannot be directly measured in the non-faradaic cases. The non-linearlity in potassium acetate was assumed to be directly proportional to the 1 M potassium chloride non-linearity. FIGS. 12A and 12B illustrate the simulation result when the applied signal has a 50% duty cycle. In FIG. 12B, the slope of the decay is steeper for the positive current than the negative current because of the rectifying characteristics of the hemolysin nanopore, which is modeled with the polynomial equations B1 and B2 in FIG. 11.

Figure 13A:
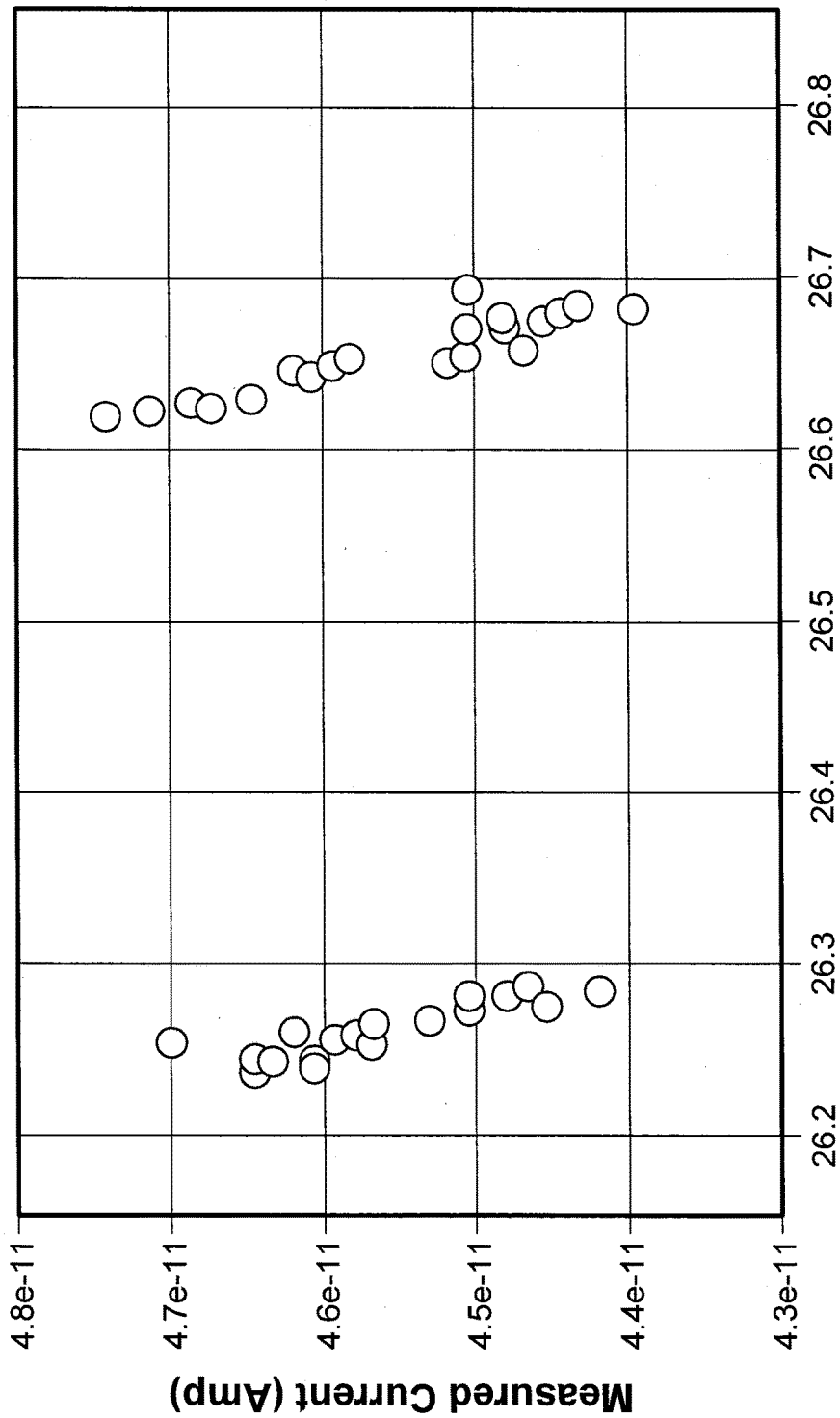
FIG. 13A illustrates the measurement current when the applied signal has a 25% duty cycle.
Figure 13B:
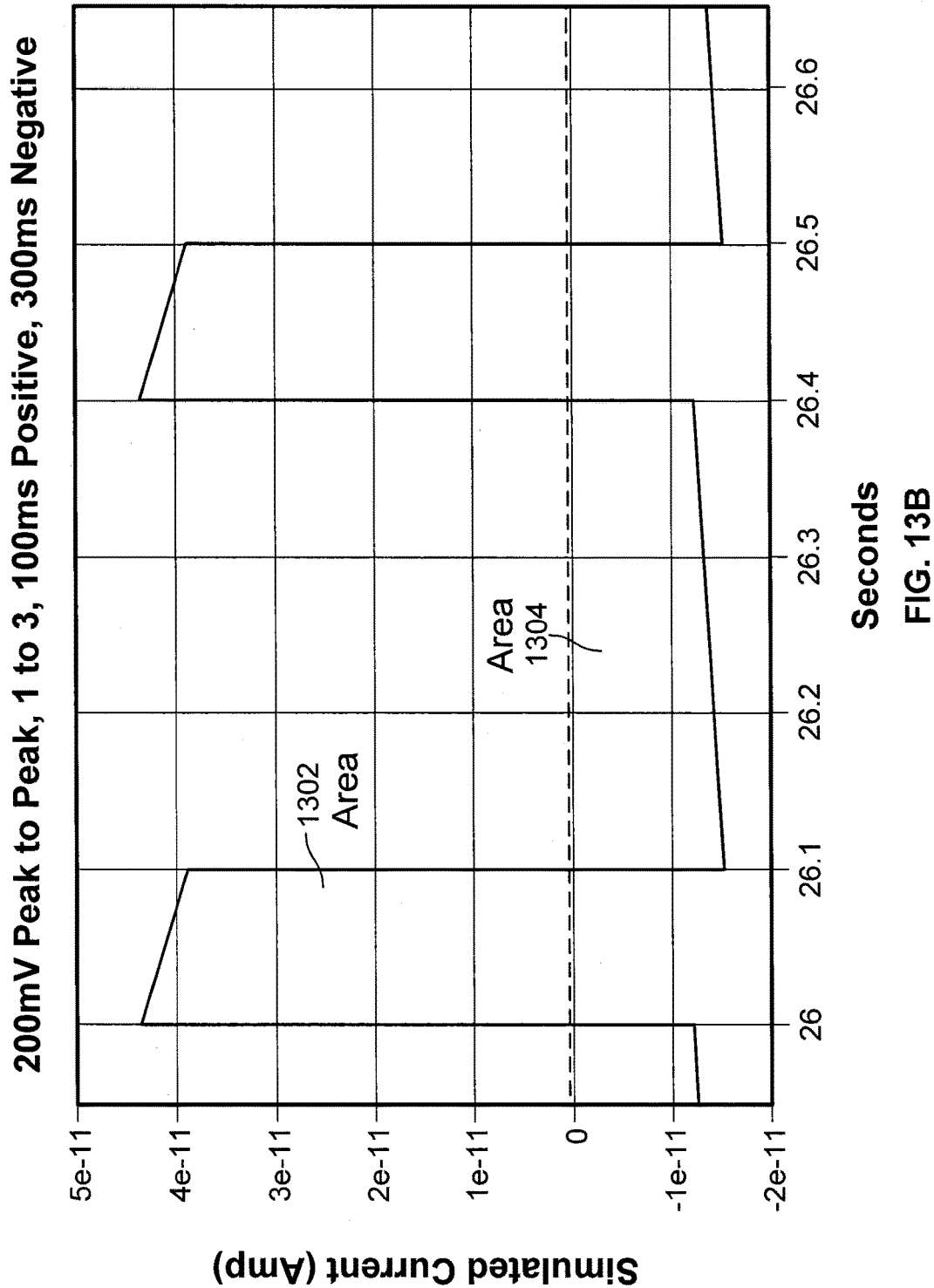
FIG. 13B illustrates the simulated current when the applied signal has a 25% duty cycle.

FIG. 13A illustrates the measurement current when the applied signal has a 25% duty cycle. FIG. 13B illustrates the simulated current when the applied signal has a 25% duty cycle. These figures illustrate that with a lower duty cycle of 25%, the magnitude of the positive current (43 pA) through the nanopore is much larger than the magnitude of the negative current (−13 pA) through the nanopore. In order to achieve no shunt resistance (no faradaic current) at steady state, the sum of the positive and negative charge through the double layer over one period of oscillation should be zero. As i=dQ/dt, where i=current and Q=charge, in a graph of current versus time, charge is the area under the curve. For example, if the area under the curve of the current versus time plot of positive polarity (area 1302 of FIG. 13B) is roughly the same as the area under the curve of the current versus time plot of negative polarity (area 1304 of FIG. 13B), then the sum of the positive and negative charge through the double layer over one period of oscillation is close to zero.

Figure 14A:
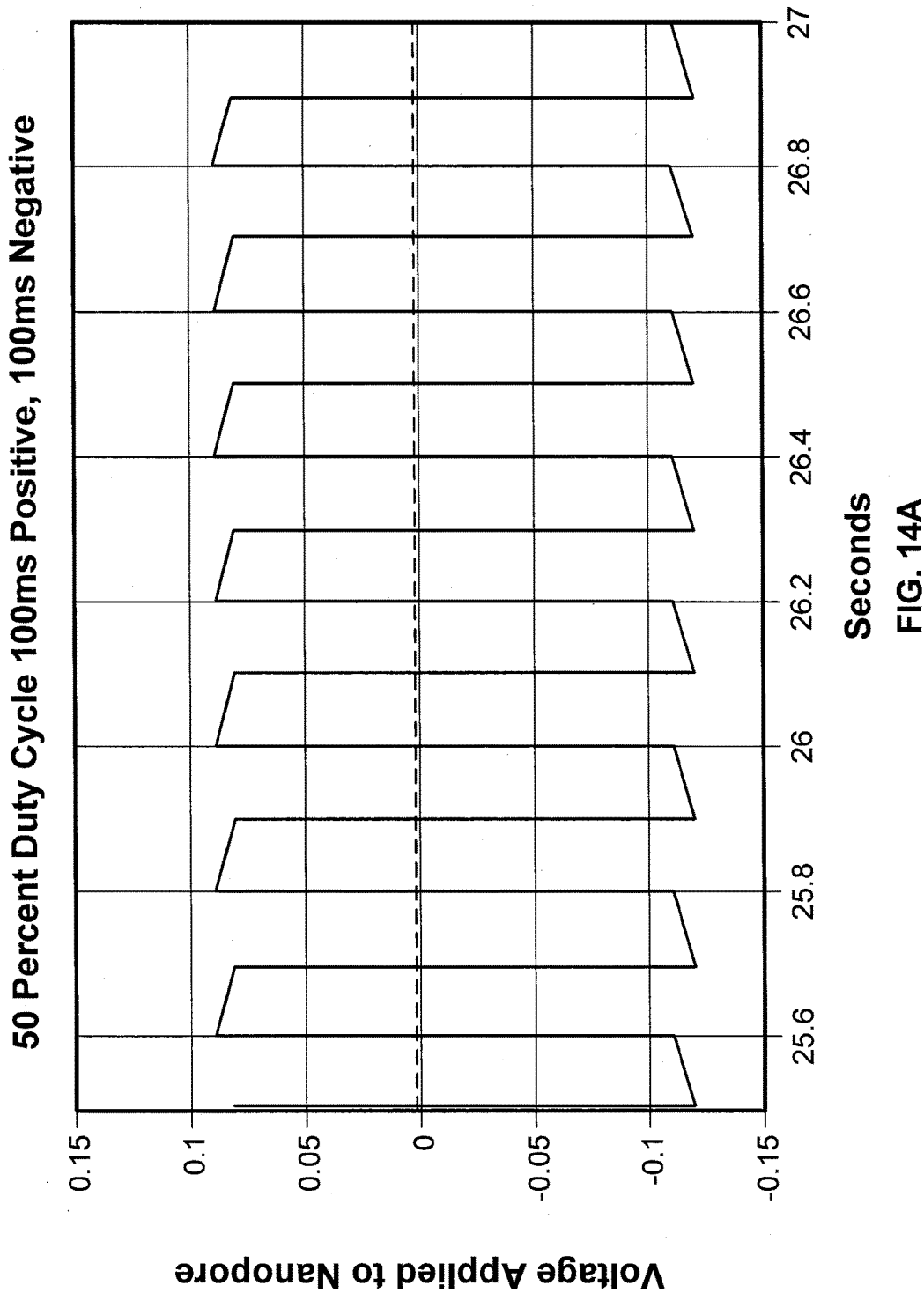
FIG. 14A illustrates the voltage applied to the nanopore versus time when the applied signal has a 50% duty cycle.
Figure 14B:
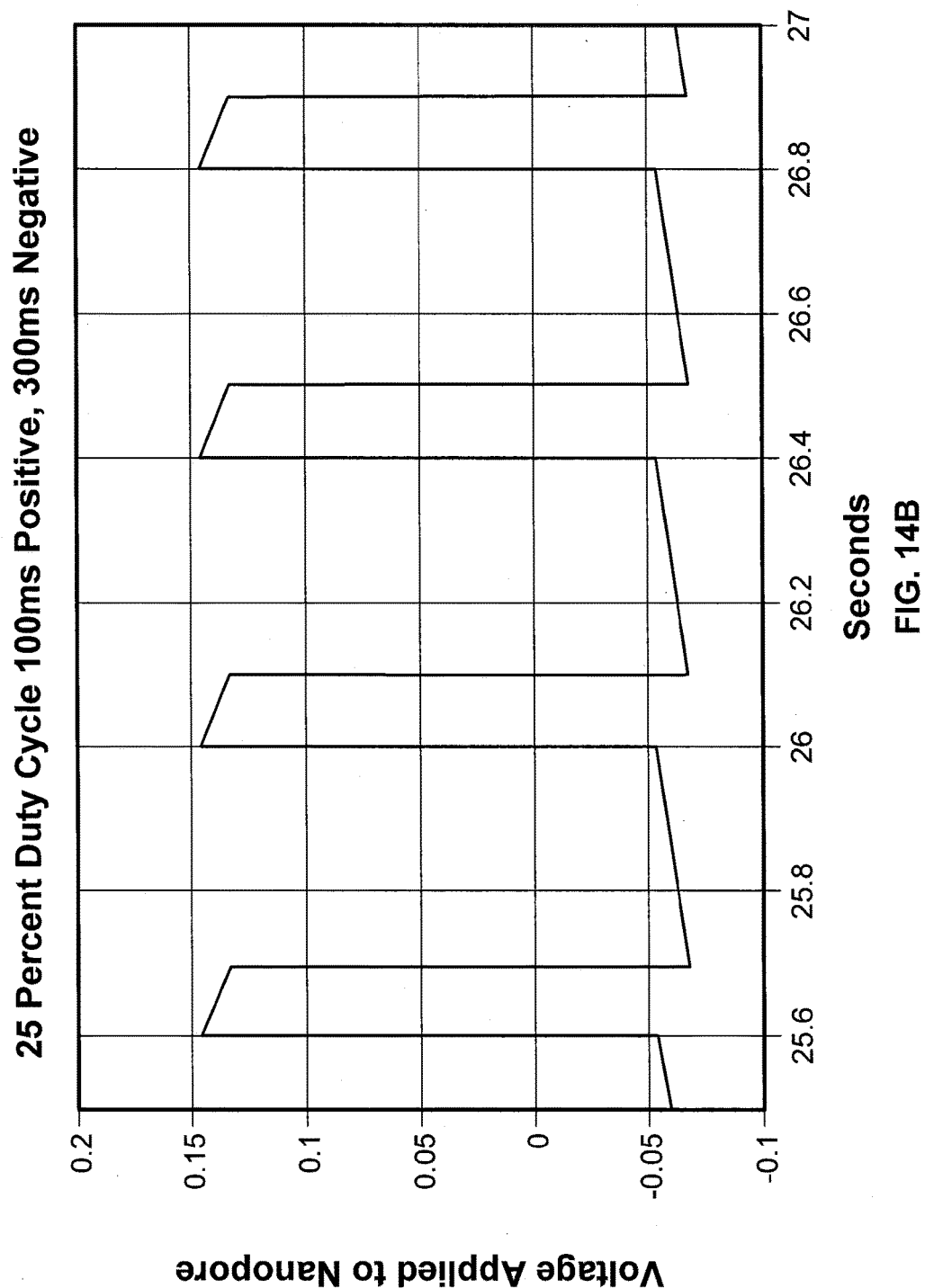
FIG. 14B illustrates the voltage applied to the nanopore versus time when the applied signal has a 25% duty cycle.

FIG. 14A illustrates the voltage applied to the nanopore versus time when the applied signal has a 50% duty cycle. FIG. 14B illustrates the voltage applied to the nanopore versus time when the applied signal has a 25% duty cycle. With a lower duty cycle in FIG. 14B, the voltage applied to the nanopore is higher, which draws the polymerase and the tag towards the nanopore with greater efficacy. With a longer duty cycle in FIG. 14A, more time is spent in reading and detecting the tag while a nucleotide specific tail is in place.

Figure 15:
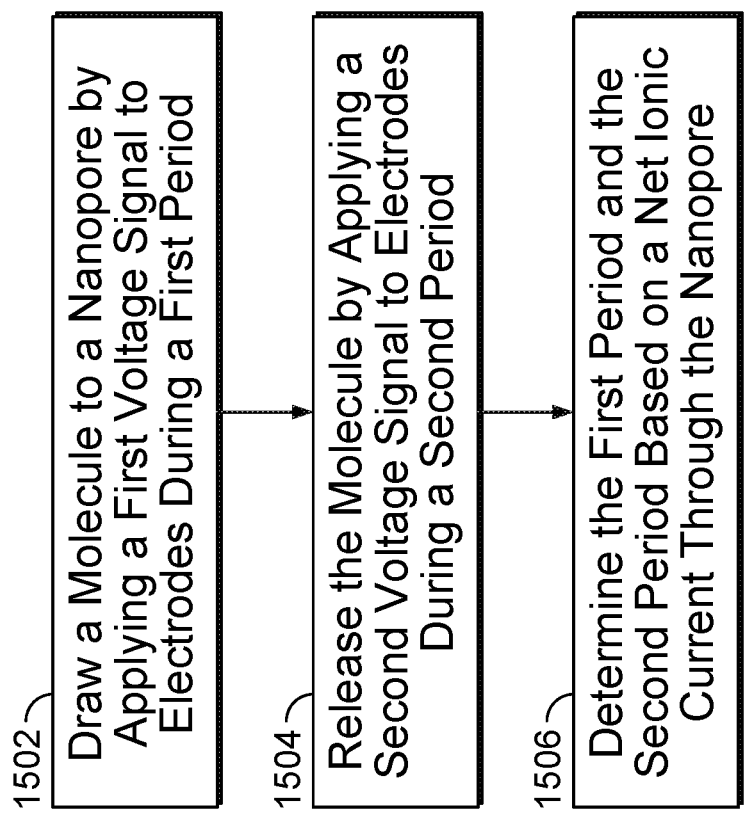
FIG. 15 illustrates an embodiment of a process for identifying a molecule.

FIG. 15 illustrates an embodiment of a process for identifying a molecule. At 1502, a molecule is drawn to a nanopore by applying a first voltage signal to a pair of electrodes (e.g., the working electrode and the counter/reference electrode) during a first period, wherein the first voltage signal causes a first ionic current through the nanopore that is indicative of a property of a portion of the molecule (e.g., a tagged nucleotide) proximate to the nanopore. For example, the four types of tagged nucleotides have different properties and when a particular type of tagged nucleotide is drawn into the nanopore, an ionic current indicative of the property flows through the nanopore.

At 1504, the molecule is released from the nanopore by applying a second voltage signal to the pair of electrodes during a second period, wherein the second voltage signal causes a second ionic current through the nanopore.

At 1506, the first period and the second period are determined based at least in part on a net ionic current through the nanopore comprising the first ionic current and the second ionic current. For example, the first period and the second period can be determined such that the net ionic current is reduced. In some embodiments, the net ionic current is reduced by setting the second voltage signal to off. When the second voltage signal is turned off, the second ionic current becomes zero and the depletion of the metal electrode is delayed as explained above. In some embodiments, the net ionic current is reduced by setting the second voltage signal to a signal with a polarity opposite from the first voltage signal. For example, alternating between the first voltage signal and the second voltage signal makes an AC signal. The second ionic current offsets the first ionic current, thus reducing the net ionic current through the nanopore. As shown in FIG. 10, the current varies as a function of duty cycle and applied voltage. Therefore, the duty cycle (i.e., the first period and the second period) can be adjusted such that the area under the curve of the first ionic current is substantially the same as the area under the curve of the second ionic current such that the sum of the positive and negative charge through the double layer over one period of oscillation (i.e., the first period and the second period) is close to zero.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of identifying a molecule, comprising:
   drawing a molecule to a nanopore by applying a first voltage signal to a pair of electrodes during a first period, wherein the first voltage signal causes a first ionic current through the nanopore that is indicative of a property of a portion of the molecule proximate to the nanopore;
   releasing the molecule from the nanopore by applying a second voltage signal to the pair of electrodes during a second period, wherein the second voltage signal causes a second ionic current through the nanopore; and
   determining the first period and the second period based at least in part on a net ionic current through the nanopore comprising the first ionic current and the second ionic current.

2. The method of claim 1, wherein determining the first period and the second period based at least in part on the net ionic current comprises determining the first period and the second period that reduce the net ionic current.

3. The method of claim 2, wherein determining the first period and the second period that reduce the net ionic current comprises setting the second voltage signal to off.

4. The method of claim 2, wherein determining the first period and the second period that reduce the net ionic current comprises setting the second voltage signal to a signal with a polarity opposite from the first voltage signal.

5. The method of claim 4, wherein the first voltage signal during the first period and the second voltage signal during the second period comprise an AC signal.

6. The method of claim 1, wherein one of the electrodes comprises a property that facilitates non-faradaic conduction.

7. The method of claim 6, wherein the one of the electrodes comprises a noble metal.

8. The method of claim 6, wherein the one of the electrodes comprises a structure that increases a surface area of the one of the electrodes.

9. The method of claim 6, wherein the one of the electrodes comprises a structure that increases a double layer capacitance.

10. The method of claim 6, wherein the one of the electrodes comprises a spongy structure.

11. The method of claim 1, wherein the first period and the second period are determined based at least in part on how fast the property of the portion of the molecule changes over time.

12. A system for identifying a molecule, comprising:
    a voltage control unit controlling a voltage source;
    a pair of electrodes coupled to the voltage source; and
    a measurement circuitry;
    wherein the voltage control unit is configured to:

draw a molecule to a nanopore by controlling the voltage source to apply a first voltage signal to the pair of electrodes during a first period, wherein the first voltage signal causes a first ionic current through the nanopore that is indicative of a property of a portion of the molecule proximate to the nanopore;

release the molecule from the nanopore by controlling the voltage source to apply a second voltage signal to the pair of electrodes during a second period, wherein the second voltage signal causes a second ionic current through the nanopore; and determine the first period and the second period based at least in part on a net ionic current through the nanopore comprising the first ionic current and the second ionic current;

and wherein the measurement circuitry is configured to measure the first ionic current.

13. The system of claim 12, wherein determining the first period and the second period based at least in part on the net ionic current comprises determining the first period and the second period that reduce the net ionic current.

14. The system of claim 13, wherein determining the first period and the second period that reduce the net ionic current comprises setting the second voltage signal to off.

15. The system of claim 13, wherein determining the first period and the second period that reduce the net ionic current comprises setting the second voltage signal to a signal with a polarity opposite from the first voltage signal.

16. The system of claim 15, wherein the first voltage signal during the first period and the second voltage signal during the second period comprise an AC signal.

17. The system of claim 12, wherein one of the electrodes comprises a property that facilitates non-faradaic conduction.

18. The system of claim 17, wherein the one of the electrodes comprises a noble metal.

19. The system of claim 17, wherein the one of the electrodes comprises a structure that increases a surface area of the one of the electrodes.

20. The system of claim 17, wherein the one of the electrodes comprises a structure that increases a double layer capacitance.

21. The system of claim 17, wherein the one of the electrodes comprises a spongy structure.

22. The system of claim 12, wherein the first period and the second period are determined based at least in part on how fast the property of the portion of the molecule changes over time.

23. The system of claim 12, wherein the molecule comprises a tagged nucleotide associated with a polymerase, and wherein the first period and the second period are determined based at least in part on a time period during which the tagged nucleotide is associated with a polymerase.

* * * * *